US006451256B1

(12) United States Patent
Sene

(10) Patent No.: US 6,451,256 B1
(45) Date of Patent: *Sep. 17, 2002

(54) METHOD FOR PRESERVING INFECTIOUS RECOMBINANT VIRUSES, AQUEOUS VIRAL SUSPENSION AND USE AS MEDICINE

(75) Inventor: Claude Sene, Mutzig (FR)

(73) Assignee: Transgene S.A., Strasbourg (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/043,187

(22) PCT Filed: Jul. 15, 1997

(86) PCT No.: PCT/FR97/01308

§ 371 (c)(1),
(2), (4) Date: Jun. 24, 1998

(87) PCT Pub. No.: WO98/02522

PCT Pub. Date: Jan. 22, 1998

(30) Foreign Application Priority Data

Jul. 16, 1996 (FR) .............................. 96 08851

(51) Int. Cl.[7] .................... B01J 19/00; C12N 15/00; C07H 21/04
(52) U.S. Cl. .................. 422/40; 435/320.1; 536/23.1
(58) Field of Search .................. 422/40; 435/320.1; 514/44; 536/23.1

(56) References Cited

U.S. PATENT DOCUMENTS

| 5,545,555 A | | 8/1996 | Racioppi | |
| 5,616,487 A | * | 4/1997 | Palsson et al. | 435/440 |
| 5,792,643 A | * | 8/1998 | Herrmann et al. | 435/235.1 |
| 5,932,223 A | * | 8/1999 | Burke et al. | 424/215.1 |

FOREIGN PATENT DOCUMENTS

| WO | 95 10601 | | 4/1995 | |
| WO | WO 95/10601 | * | 4/1995 | 435/440 |
| WO | WO 95/11664 | * | 5/1995 | 514/44 |

OTHER PUBLICATIONS

Fields et al. Concentration of adenovirus from seawater. Water Res. vol. 9(4):357–364, Apr. 1975.*
Verma et al. Gene therapy—Promises, problems and prospects. Nature, vol. 389:239–242, Sep. 1997.*
Marshall, E. Gene therapy's growing pains. Science. vol. 269:1050–1055, Aug. 1995.*
Anderson, WF Human gene therapy. Nature, vol. 392:25–30, Apr. 1998.*
Orkin et al. Report and recommendations of teh panel to assess the NIH investment in research on gene therapy, Dec. 1995.*
Inumaru et al. Stability of bovine leukemia virus antigens. Can. J. Vet. Res. vol. 51(1):95–98, Jan. 1987.*

* cited by examiner

Primary Examiner—Terry McKelvey
Assistant Examiner—William Sandals
(74) Attorney, Agent, or Firm—Burns, Doane, Swecker & Mathis, L.L.P.

(57) ABSTRACT

The present invention provides a novel method for preserving infectious recombinant viruses in frozen or liquid form, in which infectious viruses are preserved in an aqueous solution. The recombinant virus suspension comprises an aqueous sucrose solution at a concentration of 0.75 M or above, preferably between 0.75 M and 1.5 M, or more preferably at a concentration of 1 M. The preserved aqueous viral suspension further provides a medicament that can be used therapeutically or prophylactically for the treatment of a human or animal body by gene therapy.

49 Claims, 2 Drawing Sheets

METHOD FOR PRESERVING INFECTIOUS RECOMBINANT VIRUSES, AQUEOUS VIRAL SUSPENSION AND USE AS MEDICINE

This application is a national stage filing under 35 U.S.C. §371 of International Application No. PCT/FR97/01308.

The invention relates to a method of preserving infectious recombinant viruses, an aqueous viral suspension, and its use as medicament.

Live viruses are used for a variety of purposes, in particular as vaccines. They are particles which have a genome in the form of DNA or RNA containing the information which is useful for their replication, but which need to infect a host cell to synthesize proteins which they require.

Moreover, the possibility of integrating foreign genetic material into a viral genome has allowed so-called recombinant viruses to be generated which carry a gene of therapeutic interest and which are used to transfer this gene into specific cells of deficient patients. This is the principle of gene therapy.

The possibility of treating human diseases by gene therapy has passed from the stage of theoretical considerations to the stage of clinical applications within a few years. To transfer and express the therapeutic gene in the cells to be treated, the vast majority of the protocols described to date make use of viral vectors.

Due to the simplicity of their genome, retroviral vectors are currently amongst the most frequently used, even though they have a somewhat limited cloning capacity.

Adenoviruses, in turn, have several advantages which make them the vectors of choice for a wide range of applications. In effect, they infect many types of cells, are non-integrating, have low pathogenicity and can replicate in dividing or quiescent cells. By way of indication, their genome is composed of a linear double-stranded DNA molecule of approx. 36 kb which carries more than approx. thirty genes which are at the same time early genes required for viral replication (E1 to E4; E for early) and late structural genes (L1–L5; L for late).

Recombinant adenoviral vectors used for gene therapy purposes are deficient for replication to avoid them spreading in the environment and in the host organism. Generally, they lack most of the E1 region, and some lack the inflammation linked to the expression of the remaining viral genes. They can only be propagated by transcomplementation of the adenovirus functions for which they are deficient. Currently, one uses essentially the complementation line 293 (Graham et al., 1977, J. Gen. Virol. 36, 59–72) or lines derived therefrom (Yeh et al., 1996, J. Virol. 70, 559–565; Wang et al., 1995, Gene Therapy 2, 775–783; Krougliak and Graham, 1995, Human Gene Therapy 6, 1575–1586).

In particular, adenoviruses are used for treating cystic fibrosis by gene therapy (Pavirani et al., 1996, medecine/sciences 12, 25–33).

However, recombinant viruses can only be used if their viability and their infectiveness have been adequately preserved over the entire storage period.

Purified adenoviruses are traditionally preserved in saline containing 10 to 30% of glycerol (Graham et al., 1991, Methods in Molecular Biology, vol. 7, chapter 11, p. 109–127; Ed Murrey, The Human Press Inc.; Precious and Russel, Virology, a Practical Approach, 1985, chapter 9, p. 193–205; ed: BW Mahy, IRL Press, Washington DC; Kanegae et al., Jpn. J. Med. Sci. Biol., 47, 157–166, 1994 and Green et al., Methods in enzymology, vol. LVIII, p. 425–435). However, the glycerol has the disadvantage of irritating the pulmonary epithelium, which may be tricky in the case of intratracheal and intrapulmonary administration (for example for the treatment of cystic fibrosis or of cancers of the pulmonary tract). In addition, while this solution allows adenoviruses to be preserved in frozen form, it does not allow their activity to be maintained at +4° C. beyond one week.

Addition of sucrose at a low concentration (1 to 5%) to a saline has also been described (Precious et al., see above; Huyghe et al., Human Gene Therapy 6: 1403–1416, November 1995, and Rehir, Process Development and Production Issues for Viral Vectors & Vaccines, The Williamsburg Bio Processing Conference, 2nd annual meeting, Nov. 6–9, 1995), which allows long-term stability of the adenoviruses in frozen form, but at +4° C. only in the short term (Hehir, see above).

Since preservation of viruses in frozen form presents storage and transport problems, it has also been envisaged to preserve the viruses and the viral vaccines in lyophilized form. However, this technique has the disadvantage that it frequently entails loss of viral activity. To make up for this, addition of excipients such as sugars (sucrose, glucose, trehalose) allows the viral activity to be maintained in lyophilized form (WO 95/10601—Viagene and EP-0 357 709—Quadrant). The use of lactose or sucrose at low concentrations (2.5–5%) for the preservation of attenuated live viruses in lyophilized form has also been recommended (JP-88 555465—Kitasako Inst.).

None of the solutions proposed to date has permitted maintaining the activity of adenoviruses at satisfactory levels over more than 6 months while avoiding secondary problems such as problems with irritation.

The present invention overcomes the shortcomings of the prior art. It relates to a long-term preservation method for infectious recombinant viruses, both in liquid form and in frozen form, in which the recombinant viruses are preserved in an aqueous solution which comprises sucrose at high concentration.

In effect, even though the use of sucrose at high concentration has been known for a long time for the preservation of proteins or other biological products (Timasheef et al., In Protein Structure, a Practical Approach, 1989, Ed Creighton, chapter 14, p.331–345, IRL Press, Oxford, and Doebbler, Cryobiology, vol. 3, No. 1, 1966) or for the cryopreservation of live cells in liquid nitrogen (Grout et al., Tibtech, October 1990, vol. 8, p. 293–297), it has never been proposed for the reservation of viruses.

The results obtained by making use of the process according to the invention have now demonstrated a cryoprotective effect of sucrose at different storage temperatures (−80° C., −40° C., −20° C. and +4° C.) and this is more pronounced the higher the sucrose concentration.

The infectious recombinant viruses to which the present invention relates are advantageously poxviruses, adenoviruses, viruses associated with adenoviruses and retroviruses.

Within the frame of the invention, the viruses are preserved in an aqueous solution comprising sucrose at high concentration, that is to say at a concentration of above 0.75 M, preferably between 0.75 M and 1.5 M, more preferably at a concentration of 1 M.

In accordance of an advantageous embodiment of the method according to the invention, the infectious recombinant viruses gain in stability when the aqueous solution used has a basic pH of between 8 and 9, preferably 8.5.

Thus, the aqueous solution of which use is made within the frame of the present invention can be a buffer solution selected from amongst Tris buffer, and triethanolamine, diethanolamine, borate/HCl, glycine/NaOH, EPPS [N-(2-hydroxyethyl)piperazine-N'-(3-propanesulfonic), acid], bicine, TAPS [N-Tris-(hydroxymethyl)-methyl-3-aminopropanesulfonic acid] and tricine solutions.

Advantageously, it is furthermore possible to stabilize the capsid or viral coat of the viruses preserved according to the invention by adding, to the aqueous solution used, at least one salt of a divalent cation selected from amongst $MgCl_2$, $CaCl_2$ and $MnCl_2$, with $MgCl_2$ being preferred.

Within the frame of the present invention, the salt of the divalent cation is used at a concentration of between 0.1 and 5 mM, preferably between 0.5 and 2 mM, ore preferably in the order of 1 mM.

According to an advantageous embodiment of the method according to the invention, the viruses are preserved in a buffer solution comprising 10 mM Tris-HCl buffer, 1 mM $MgCl_2$, 1 M sucrose, pH 8.5.

Preservation of the viruses can be improved even further by using at least one stabilizer selected from amongst salts, preferably monovalent salts such as NaCl or KCl, which impart an ionic strength to the solution, amino acids such as Gly, Leu, Lys, Arg, Asp, Val, Glu and compounds which act on the surface tension such as TWEEN 80 (polysorbate 80) or TRITON X-100, (nonaethylene glycol octyl phenol ether), it being possible to use the latter items alone or in the presence of salts.

By way of stabilizer, the NaCl is advantageously used at a concentration of between 0.05 and 1 M, preferably between 0.1 and 0.5 M, more preferably between 0.1 and 0.3 M, the concentration considered as optimum being 0.15 M, and the TWEEN 80 is used at a concentration between 0.001 and 0.5% by weight based on the total solution (that is to say between 10 mg/i and 5 g/l), preferably between 0.002 and 0.2% by weight, more preferably in the order of 0.005% by weight.

According to a preferred embodiment, the method according to the invention makes use of an aqueous solution of a pH of approximately 8.5 comprising 10 mM Tris-HCl, 1 MM $MgCl_2$, 0.9% (or 150 mM) NaCl, 50 mg/l (0.05%) TWEEN 80 and 1M sucrose 1.

In addition, the infectious recombinant viruses preserved in accordance with the method according to the invention may be lyophilized.

The invention furthermore relates to an aqueous suspension of infectious recombinant viruses in an aqueous sucrose solution at high concentration as described above.

The aqueous suspension according to the invention advantageously comprise $10^6$ to $10^{13}$ pfu/ml infectious recombinant virus.

The present invention also relates to a pharmaceutical composition comprising an aqueous suspension of infectious recombinant viruses such as described above or obtained by making use of the preservation method according to the invention, in association with a pharmaceutically acceptable vehicle. It can be administered by the systemic route, in particular the subcutaneous, intravenous, intracardiac, intramuscular, intraperitoneal, intragastric, intratumoral, intrapulmonary, intranasal or intratracheal route. Administration can be as a single dose or a dose which is repeated once or more than once after a certain interval. Also, the formulation may include other compounds such as an adjuvant or pharmaceutically acceptable excipient. In particular, a composition according to the invention is intended for the preventative or curative treatment of diseases such as genetic diseases (hemophilia, cystic fibrosis, diabetes, Duchenne's and Becker's myopathy, . . . ), cancers, viral diseases (various forms of hepatitis, AIDS, . . . ) and recurrent diseases (infections provoked by herpesvirus, human papilloma virus, . . . ).

Finally, the present invention relates to therapeutic or prophylactic use of an aqueous suspension of infectious recombinant viruses as described above or obtained by making use of the preservation method according to the invention for the preparation of a medicament intended for the treatment of the human or animal body by gene therapy. The aqueous suspension may be administered directly in vivo (for example by intravenous injection, intramuscular injection, into an accessible tumor, into the lungs by means of an aerosol, . . . ). The ex-vivo approach may also be adopted, and this consists in removing cells from the patient (bone marrow stem cells, peripheral-blood lymphocytes, muscle cells, . . . ), infecting them with the aqueous suspension according to the invention following techniques known in the art, and readministering them to the patient.

Figure 1:
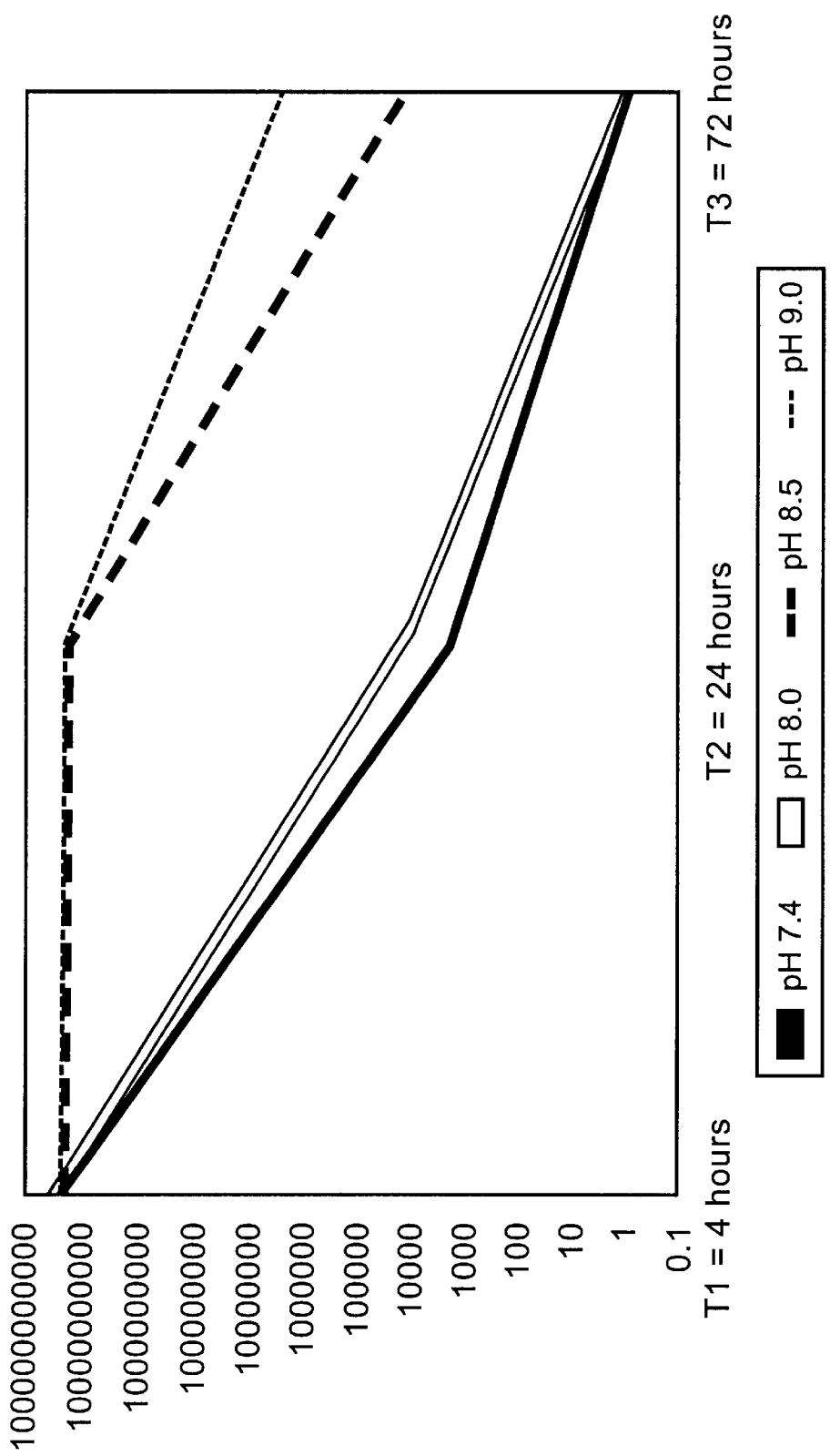
FIG. 1 illustrates the pH effect of the sucrose solution on viral stability.

Other features of the invention will become apparent in the light of the examples which follow.

MATERIALS AND METHODS

The examples which follow make use of a recombinant adenoviral vector which expresses either the marker gene LacZ, which encodes E. coli β-galactosidase, or the therapeutic gene CF, which encodes the CFTR (Cystic Fibrosis Transmembrane conductance Regulator) protein, for which the patients which suffer from cystic fibrosis are deficient. By way of indication, the vector is obtained from the adenovirus type 5 (Ad5) genome from which the regions E1 and E3 have been deleted and comprises an expression cassette of the marker or therapeutic gene integrated instead of the E1 region (Stratford-Perricaudet et al., 1992, J. Clin. Invest. 90, 626–630; Rosenfeld et al., 1992, Cell. 68, 143–155). It can be propagated in line 293 (Graham et al., 1977, J. Gen. Virol, 36, 59–72), which complements the E1 function which is essential for viral replication. By way of indication, line 293 is derived from the human embryonic kidney and is the result of integrating, into its chromosomes, the 5' end of the Ad5 genome (11%). The 293-cells are available from ATCC (CRL1573) and are cultured according to the supplier's recommendations, or as recommended in the literature.

A primary viral stock is made up in the conventional manner in 293-cells which have been transfected with the above-described adenoviral vector. The production of infectious viral particles harvested after cell lysis is checked by consecutive freezing/defrosting cycles, the titer of the viral preparation by the agar method (Graham and Prevec, 1991, Methods in Molecular Biology, vol. 7, p. 109–128; Ed: E. J. Murey, The Human Press Inc.) and expression of the marker gene by Xgal (4-chloro-5-bromo-3-indolyl-β-galactosidase)—coloration following the method of Sanes et al. (1986, EMBO, J. 5, 3133–3142) or of the CF-gene by Western blot with the aid of specific antibodies (Dalemans et al., 1992, Experimental Cell Research 201, 235–240). Before the viral preparation is used, it may be subjected to density-gradient concentration and purification.

EXAMPLE 1

Effect of pH on Viral Stability

A viral suspension is prepared as follows.

The 293-cells are cultured in CELLCUBE (Costar) in a GMEM-medium supplemented with 7% of fetal calf serum (FCS). Upon reaching confluence, they are infected with an aliquot of the primary stock of the adenoviral vector which expresses the CF gene at an m.o.i. (multiplicity of infection) of 2. Thirty hours after infection, the weakened cells are detached by mechanical stirring or with the aid of a chemical agent and harvested by low-speed centrifugation (3500 rpm (revolutions per minute) for 8 minutes). They are lysed, and the viral particles are freed by 3 freezing/defrosting cycles, and cell debris is eliminated by centrifugation (3500 rpm for 8 minutes). The virus is purified from the supernatant by two ultracentrifugations with cesium chloride (CsCl), the first on CsCl cushions of a density d=1.25 and d=1.40, respectively (141,000 g for 2 hours), and the second on an autonomously formed gradient using a CsCl-solution of a density d=1.34 (231,000 g for 18 hours).

The viral band is recovered, its titer is determined ($2 \times 10^{11}$ pfu), and the preparation is divided into 4 batches which are dialyzed at 4° C. against 4 times 250 ml of 10 mM Tris buffer, 1 mM $MgCl_2$, 10% glycerol of, increasing pH: pH 7.4, 8, 8.5 and 9, respectively. Viral stability in the different buffers of the formulation is studied in parallel (accelerated stability study). To this end, each batch is packaged into 1 ml cryotubes containing 100 µl of suspension in each case. The samples are incubated at 37° C. and removed at $t_0$ and after 4, 24 and 72 hours of incubation, respectively. They are preserved at −20° C. until titration. The virus titer is determined by the agar method by reinfecting 293-cells with different dilutions of the test sample. The results are given in pfu (plaque-forming units)/ml.

The results shown in FIG. 1 show that the formulation with alkaline pH preserves the infectious activity of the adenoviruses. In effect, the titer of the preparations formulated in buffers of pH 8.5 and 9 are stable over 24 hours at 37° C. and then decrease progressively in the course of time. On the other hand, the viruses placed into a buffer of pH 7.4 and 8 lose their infectious potential from the beginning of incubation at 37° C. After 24 hours, the titers are already very low ($10^3$ to $10^4$ pfu/ml versus in the order of $10^{10}$ at the beginning) and the viruses are virtually no longer infectious after 72 hours.

EXAMPLE 2

Effect of Sucrose Concentration on Viral Stability

A viral suspension is prepared as described in Example 1 with the following modifications:

the cells are infected with the adenoviral vector which expresses the LacZ gene;

the infected cells are lysed mechanically (Silverson homogenizer; reference L4R);

the CsCl-gradient ultracentrifugations are effected with the aid of fixed-angle rotors (235,000 g for 2 h for the first one and 435,000 g for 18 hours for the second one);

dialysis is replaced by a gel filtration chromatography step with the aid of a TRISACRYL GF05 LS matrix (Biosepra, reference 259161), which allows desalination of the solution by eliminating CsCl;

the viruses are formulated in a solution of 10 mM Tris-HCl, 1 MM MgCl, and 1 M sucrose, pH 8.5, and are then divided into 5 batches by diluting them 1/20 in the buffers indicated hereinbelow, which have been filtered beforehand on a membrane of porosity 0.22 µm Batch 1) 10 mM Tris-HCl 1 mM $MgCl_2$ 1M sucrose pH 8.5

Batch 2) 10 mM Tris-HCl 1 mM $MgCl_2$ 0.75 M sucrose pH 8.5

Batch 3) 10 mM Tris-HCl 1 mM $MgCl_2$ 0.5 M sucrose pH 8.5

Batch 4) 10 mM Tris-HCl 1 mM $MgCl_2$ 0.25 M sucrose pH 8.5

Batch 5) 10 Mm Tris-HCl 1 mM $MgCl_2$ 0 M sucrose pH 8.5

Each of the batches has a starting titer of approx. $10^{10}$ pfu/ml. Viral stability in measured under accelerated conditions (37° C.) on aliquots which are removed at regular intervals.

The results are shown in Table 1 below:

TABLE 1

Effect of source concentration on viral stability at 37° C.

| Titer (pfu/ml) Time | 1 | 2 | 3 | 4 | 5 |
|---|---|---|---|---|---|
| 8 h | $1.27 \times 10^{10}$ | $1.25 \times 10^{17}$ | $1.22 \times 10^{18}$ | $1.32 \times 10^9$ | $2.77 \times 10^7$ |
| 24 h | $8.5 \times 10^8$ | $5.02 \times 10^9$ | $1.47 \times 10^8$ | $<10^4$ | $<10^4$ |
| 48 h | $3.82 \times 10^9$ | $4 \times 10^7$ | $3.25 \times 10^4$ | $<10^4$ | $<10^2$ |
| 72 h | $2.37 \times 10^9$ | $7.5 \times 10^5$ | $1.5 \times 10^5$ | $<10^8$ | $<10^8$ |
| 1 week | $4.5 \times 10^4$ | $<10^4$ | $<10^4$ | $<10^3$ | $<10^2$ |
| 2 weeks | $2.5 \times 10^3$ | 5 | <10 | <10 | <10 |
| 1 month | <10 | <10 | <10 | <10 | <10 |

1 10 mM Tris-HCl, 1 mM $MgCl_2$, 1M sucrose, pH 8.5
2 10 mM Tris-HCl, 1 mM $MgCl_2$, 0.75 sucrose, pH 8.5
3 10 mM Tris-HCl, 1 mM $MgCl_2$, 0.5M sucrose, pH 8.5
4 10 mM Tris-HCl, 1 mM $MgCl_2$, 0.25 sucrose, pH 8.5
5 10 mM Tris-HCl, 1 mM $MgCl_2$, 0M sucrose, pH 8.5

This study indicates that the higher the sucrose concentration, the better the preservation of viral activity (batch 1 more stable than batch 2, which, in turn, is more stable than batch 3, etc.). In the absence of sucrose (batch 5), the infectious potential drops very rapidly (reduction by a factor of 5000 after 8 hours of incubation). In the presence of 0.25 M (batch 4), the titer is reduced rapidly, but to a lesser degree (reduction by a factor of 10 after 8 hours at 37° C.). By raising the sucrose concentrations further (batches 1, 2 and 3), the titer is maintained over more than 8 hours and then decreases progressively with incubation. However, the decrease is minimal when the sucrose concentration reaches 1 M (batch 1).

EXAMPLE 3

Long-term Stability Study Into the Formulation Buffer 10 mM Tris-HCl, 1 M MgCl$_2$, 1 M Sucrose, pH 8.5

The study is carried out using the viral suspension obtained in Example 2, of which the stability under long-term conditions at +4° C. and −20° C. is studied. The virus titer is monitored over time by means of agar titration, and the results shown in Table 2 hereinbelow show a stability of the viral preparations formulated in the presence of 1 M sucrose at pH 8.5 over at least 6 months.

TABLE 2

Stability study at +4° C. and −20° C. of a viral preparation formulated in 1M sucrose.
Virus titers in pfu/ml:

| Time | +4° C. | −20° C. |
|---|---|---|
| $t_0$ | | $4.8 \times 10^9$ |
| 1 month | $1 \times 10^{10}$ | $9.75 \times 10^9$ |
| 2 months | $9.25 \times 10^9$ | $1.38 \times 10^{10}$ |
| 3 months | $1.32 \times 10^{10}$ | $1.05 \times 10^{10}$ |
| 6 months | $1.1 \times 10^{10}$ | $1.0 \times 10^{10}$ |
| 1 year | $3.7 \times 10^9$ | $5.0 \times 10^9$ |

The formulation buffer with 1 M sucrose was also compared with the conventional buffer (10 mM Tris-HCl, 1 mM MgCl$_2$, 10% of glycerol, pH 7.4). This study was carried out at +4° C. on a viral suspension which was diluted to a final titer of approx. $10^{10}$ pfu/ml in 2 types of buffer. The results are shown in Table 3 hereinbelow.

TABLE 3

Stability study at +4° C. of a viral preparation formulated in 1M sucrose or m 10% of glycerol

| | Virus titers in pfu/ml | |
|---|---|---|
| Time | 1 | 2 |
| t = 0 | $2.5 \times 10^{10}$ | $1.0 \times 10^{10}$ |
| t = 1 month | ND | $1.2 \times 10^3$ |
| t = 3 months | $2.5 \times 10^{10}$ | $3.8 \times 10^3$ |
| t = 6 months | $2.6 \times 10^{10}$ | ND |

1 10 mM Tris, 1 mM MgCl$_2$, 1M sucrose, pH 8.5
2 10 mM Tris, 1 mM MgCl$_2$, 10% of glycerol, pH 7.4

The virus titer is stable over more than 6 months at +4° C. when the formulation buffer comprises 1 M sucrose and when the pH is weakly alkaline, whereas it decreases from the first month when the viruses are placed at neutral pH in the presence of 10% of glycerol.

EXAMPLE 4

Optimization of the Formulation Buffer

The viral suspension obtained in Example 2 is divided into 2 batches which are diluted 1/20 in the formulation buffer used for batch 1), either not supplemented or in the presence of 50 mg/l TWEEN 80 (0.005%) and 150 mM NaCl. The stability is analyzed at 37° C. and at 4° C.

Figure 2:
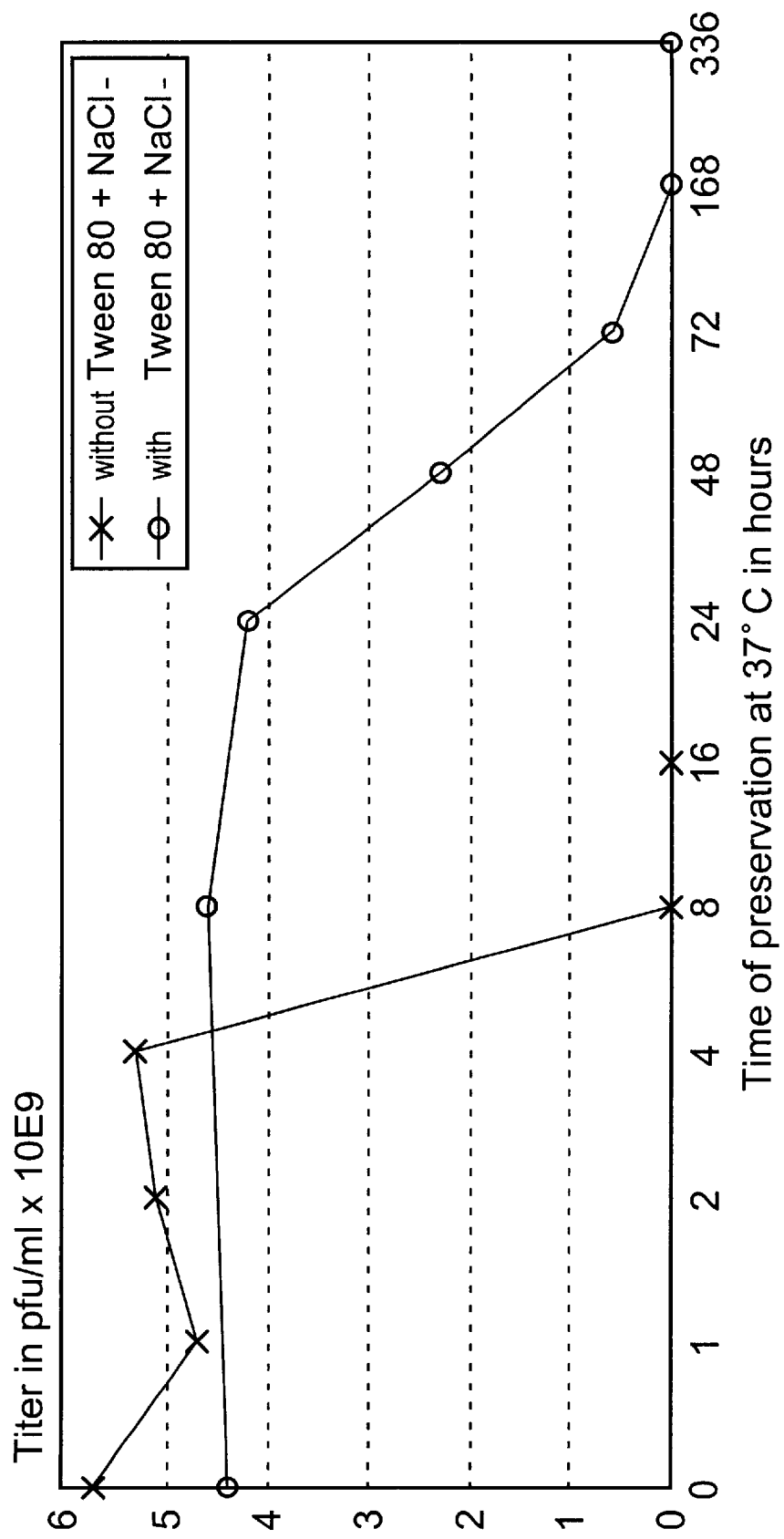
FIG. 2 illustrates the effect of adding Tween 80 and NaCl to the sucrose solution. The unit of the ordinate is expressed in pfu/ml.

The accelerated-stability results (FIG. 2) show that an addition of preservatives such as Tween 80 and salt further improves the stability of the virus formulated in 10 mM Tris-HCl buffer, 1 mM MgCl$_2$, 1 M sucrose, pH 8.5. When these are present, the infectious activity is maintained over 24 hours at 37° C., instead of 8 hours in their absence.

Furthermore, the presence of 2 preservatives does not adversely affect the stability of the viral preparation at +4° C. since the titer proves stable over more than 6 months.

EXAMPLE 5

Stability in Formulation Buffer 10 mM Tris-HCl, 1 mM MgCl$_2$, 0.9% of NaCl, 50 mg/l of TWEEN 80 and 1 M Sucrose, pH 8.5

A viral suspension as described in Example 2, formulated in a solution of 10 m Tris-HCl, 1 mM MgCl$_2$ and 1 M sucrose is diluted 1/20 in the following formulation buffer:

| Tris-HCl | 10 mM |
|---|---|
| MgCl$_2$ | 1 mM |
| NaCl | 0.9% (150 mM) |
| TWEEN 80 | 50 mg/l |
| Sucrose | 1M |
| pH 8.5 | |

The sample is packaged into 1 ml cryotubes each of which contains 100 μl of viral suspension. The cryotubes are preserved at +4° C., and the virus titers are determined at to and regularly over time in the course of 1 year. The samples are kept at −20° C. until titration. The results are shown in Table 4 below and show that the virus is stable over at least 1 year.

TABLE 4

| Preservation time at 4° C. | Titer in pfu/ml |
|---|---|
| $t_0$ | $5.5 \times 10^9$ |
| 2 weeks | $5.6 \times 10^9$ |
| 1 month | $23 \times 10^9$ |
| 2 months | $4 \times 10^9$ |
| 3 months | $5.6 \times 10^9$ |
| 6 months | $4.5 \times 10^9$ |
| 1 year | $2.5 \times 10^9$ |

What is claimed is:
1. A method of preserving infectious recombinant viruses in liquid form, comprising preserving infectious recombinant viruses in an aqueous solution, wherein said aqueous solution comprises sucrose at a concentration of above 0.75 M at a pH between 8 and 9 and said preserved recombinant viruses remain infectious.

2. The method of claim 1, wherein the viruses are adenoviruses or retroviruses.

3. The method of claim 1, wherein the aqueous solution comprises 10 mM Tris-HCl buffer, 1 mM MgCl$_2$, and 1 M sucrose at a pH of approximately 8.5.

4. The method of claim 1, wherein the aqueous solution is at a temperature of +4° C. or less.

5. The method of claim 1, wherein the preserved infectious recombinant viruses in the aqueous solution are lyophilized.

6. The method of claim 1, wherein the pH of the aqueous solution is approximately 8.5.

7. The method of claim 1, wherein the aqueous solution is a buffer solution.

8. The method of claim 7, wherein the buffer is selected from the group consisting of Tris-HCl, triethanolamine, diethanolamine, borate/HCl, glycine/NaOH, EPPS (N-(2-hydroxyethyl) piperazine-N'-(3-propanesulfonic acid)), bicine, TAPS (N-Tris-(hydroxymethyl)methyl-3-aminopropanesulfonic acid) and tricine.

9. The method of claim 1, wherein the aqueous solution additionally comprises at least one salt of a divalent cation selected from the group consisting of $MgCl_2$, $CaCl_2$, and $MnCl_2$.

10. The method of claim 9, wherein the salt of the divalent cation is present in the aqueous solution at a concentration of between 0.1 and 5 mM.

11. The method of claim 1, wherein the aqueous solution comprises at least one stabilizer selected from the group consisting of monovalent salts, amino acids, and surfactants.

12. The method of claim 11, wherein the monovalent salt is NaCl or KCl.

13. The method of claim 12, wherein the monovalent salt is present in the aqueous solution at a concentration of between 0.05 and 1 M.

14. The method of claim 11, wherein the surfactant is polysorbate 80 or nonaethylene glycol octyl phenol ether.

15. The method of claim 14, wherein polysorbate 80 is present in the aqueous solution at a concentration of between 0.001 and 0.5% by weight based on the total solution.

16. The method of claim 15, wherein the aqueous solution comprises 10 mM Tris-HCl buffer, 1 mM $MgCl_2$, 150 mM NaCl, 0.05% polysorbate 80 and 1 M sucrose at a pH of approximately 8.5.

17. An aqueous suspension of infectious recombinant viruses form comprising an aqueous sucrose solution at a concentration of above 0.75 M and a pH between 8 and 9.

18. The aqueous suspension of claim 17, wherein the viruses are adenoviruses or retroviruses.

19. The aqueous suspension of claim 17, wherein the solution comprises 10 mM Tris-HCl buffer, 1 mM $MgCl_2$ and 1 M sucrose at a pH of approximately 8.5.

20. The aqueous suspension of claim 17, comprising from $10^6$ to $10^{13}$ pfu/ml infectious recombinant viruses.

21. A pharmaceutical composition comprising the aqueous suspension of claim 17, in association with a pharmaceutically acceptable vehicle.

22. The aqueous suspension of claim 17, wherein the pH of the aqueous solution is approximately 8.5.

23. The aqueous suspension of claim 17, wherein the solution is a buffer solution.

24. The aqueous suspension of claim 23, wherein the buffer is selected from the group consisting of Tris-HCl buffer, triethanolamine, diethanolamine, borate/HCl, glycine/NaOH, EPPS (N-(2-hydroxyethyl) piperazine-N'-(3-propanesulfonic acid)), bicine, TAPS (N-Tris-(hydroxymethyl)methyl-3-aminopropanesulfonic acid) and tricine.

25. The aqueous suspension of claim 17, wherein the solution additionally comprises at least one salt of a divalent cation selected from the group consisting of $MgCl_2$, $CaCl_2$ and $MnCl_2$.

26. The aqueous suspension of claim 25, wherein the salt of the divalent cation is present in the aqueous solution at a concentration of between 0.1 and 5 mM.

27. The aqueous suspension of claim 17, wherein the solution comprises at least one stabilizer selected from the group consisting of monovalent salts, amino acids and surfactants.

28. The aqueous suspension of claim 27, wherein the monovalent salt is NaCl or KCl.

29. The aqueous suspension of claim 28, wherein the monovalent salt is present in the solution at a concentration of between 0.05 and 1 M.

30. The aqueous suspension of claim 27, wherein the surfactant is polysorbate 80 or nonaethylene glycol octyl phenol ether.

31. The aqueous suspension of claim 30, wherein polysorbate 80 is present in the solution at a concentration of between 0.001 and 0.5% by weight based on the total solution.

32. The aqueous suspension of claim 31, comprising 10 mM Tris-HCl buffer, 1 mM $MgCl_2$, 150 mM NaCl, 0.05% polysorbate 80 and 1 M sucrose at a pH of approximately 8.5.

33. A method of preserving infectious recombinant viruses in frozen form, comprising preserving infectious recombinant viruses in an aqueous solution, wherein said aqueous solution comprises sucrose at a concentration of above 0.75 M and the pH of the aqueous solution is between 8 and 9, and the preserved recombinant viruses remain infectious.

34. The method of claim 33, wherein the viruses are adenoviruses or retroviruses.

35. The method of claim 33, wherein the aqueous solution comprises 10 mM Tris-HCl, 1 mM $MgCl_2$ and 1 M sucrose, at a pH of approximately 8.5.

36. The method of claim 33, wherein the viruses in the aqueous solution are preserved at a temperature of approximately −20° C.

37. The method of claim 33, wherein the viruses in solution are then lyophilized.

38. The method of claim 33, wherein the pH of the aqueous solution is approximately 8.5.

39. The method of claim 33, wherein the aqueous solution is a buffer solution.

40. The method of claim 39, wherein the buffer is selected from the group consisting of Tris-HCl, triethanolamine, diethanolamine, borate/HCl, glycine/NaOH, EPPS (N-(2-hydroxyethyl) piperazine-N'-(3-propanesulfonic acid)), bicine, TAPS (N-Tris-(hydroxymethyl)-methyl-3-aminopropanesulfonic acid) and tricine.

41. The method of claim 33, wherein the aqueous solution additionally comprises at least one salt of a divalent cation selected from the group consisting of $MgCl_2$, $CaCl_2$, and $MnCl_2$.

42. The method of claim 41, wherein the salt of the divalent cation is present in the aqueous solution at a concentration of between 0.1 and 5 mM.

43. The method of claim 33, wherein the aqueous solution comprises at least one stabilizer selected from the group consisting of monovalent salts, amino acids, and surfactants.

44. The method of claim 43, wherein the monovalent salt is NaCl or KCl.

45. The method of claim 44, wherein the monovalent salt is present in the aqueous solution at a concentration of between 0.05 and 1.0 M.

46. The method of claim 43, wherein the surfactant is polysorbate 80 or nonaethylene glycol octyl phenol ether.

47. The method of claim 46, wherein polysorbate 80 is present in the aqueous solution at a concentration of between 0.001 and 0.5% by weight based on the total solution.

48. The method of claim 47, wherein the aqueous solution comprises 10 mM Tris-HCl buffer, 1 mM $MgCl_2$, 150 mM NaCl, 0.05% polysorbate 80 and 1 M sucrose at a pH of approximately 8.5.

49. A method of preserving infectious recombinant viruses in frozen form comprising preserving infectious recombinant viruses in an aqueous solution, wherein said aqueous solution comprises sucrose at a concentration of above 0.75 M and the pH of the aqueous solution is approximately 8.5, and the preserved recombinant viruses remain infectious.

* * * * *